United States Patent
Brown et al.

(10) Patent No.: US 6,538,167 B1
(45) Date of Patent: *Mar. 25, 2003

(54) PROCESS FOR PRODUCING LIGHT OLEFINS

(75) Inventors: Stephen H. Brown, Princeton, NJ (US); William A. Weber, Burlington, NJ (US); Reuel Shinnar, Great Neck, NY (US); Khushrav E. Nariman, Sugar Land, TX (US); Larry A. Green, Mickleton, NJ (US); Mark F. Mathias, Pitsford, NY (US); David H. Olson, Pennington, NJ (US); Robert A. Ware, Wyndmoor, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/687,859

(22) Filed: Oct. 13, 2000

Related U.S. Application Data

(63) Continuation-in-part of application No. 09/547,093, filed on Apr. 11, 2000, now abandoned, which is a continuation-in-part of application No. 09/055,486, filed on Apr. 6, 1998, now Pat. No. 6,046,372, which is a continuation-in-part of application No. 08/725,277, filed on Oct. 2, 1996, now abandoned.

(51) Int. Cl.[7] ............................. C07C 1/20; C07C 1/207
(52) U.S. Cl. ..................................... 585/640; 585/639
(58) Field of Search ................................. 585/640, 639

(56) References Cited

U.S. PATENT DOCUMENTS

| | | | |
|---|---|---|---|
| 3,702,886 A | 11/1972 | Argauer et al. | 423/328 |
| 3,709,979 A | 1/1973 | Chu | 423/328 |
| 3,832,449 A | 8/1974 | Rosinski et al. | 423/328 |
| 4,016,218 A | 4/1977 | Haag et al. | 260/671 R |
| 4,016,245 A | 4/1977 | Plank et al. | 423/328 |
| 4,025,571 A | 5/1977 | Lago | 260/668 |
| 4,025,572 A | 5/1977 | Lago | 260/668 |
| 4,025,575 A | 5/1977 | Chang et al. | 260/682 |
| 4,038,889 A | 8/1977 | Lindow et al. | 74/866 |
| 4,076,842 A | 2/1978 | Plank et al. | 423/328 |
| 4,079,095 A | 3/1978 | Givens et al. | 260/682 |
| 4,083,888 A | 4/1978 | Caesar et al. | 200/682 |
| 4,083,889 A | 4/1978 | Caesar et al. | 260/682 |
| 4,296,266 A | 10/1981 | Wunder et al. | 585/640 |
| 4,324,940 A | 4/1982 | Dessau | 585/466 |
| 4,356,338 A | 10/1982 | Young | 585/407 |
| 4,374,295 A | 2/1983 | Lee | 585/640 |
| 4,375,573 A | 3/1983 | Young | 585/467 |
| 4,423,273 A | 12/1983 | Hoelderich et al. | 585/640 |
| 4,433,188 A | 2/1984 | Hoelderich et al. | 585/640 |
| 4,433,189 A | 2/1984 | Young | 585/640 |
| 4,434,314 A | 2/1984 | Hoelderich et al. | 585/640 |
| 4,440,871 A | 4/1984 | Lok et al. | 502/214 |
| 4,441,990 A | 4/1984 | Huang | 208/111 |
| 4,480,145 A | 10/1984 | Brennan et al. | 585/640 |
| 4,496,786 A | 1/1985 | Santilli et al. | 585/640 |
| 4,499,314 A | 2/1985 | Seddon et al. | 585/408 |
| 4,499,327 A | 2/1985 | Kaiser | 585/640 |
| 4,547,616 A | 10/1985 | Avidan et al. | 585/640 |
| 4,550,217 A | 10/1985 | Graziani et al. | 585/324 |
| 4,582,815 A | 4/1986 | Bowes | 502/64 |
| 4,616,098 A | 10/1986 | Hoelderich et al. | 585/640 |
| 4,665,268 A | 5/1987 | Lee et al. | 585/640 |
| 4,677,242 A | 6/1987 | Kaiser | 585/638 |
| 4,677,243 A | 6/1987 | Kaiser | 585/638 |
| 4,698,452 A | 10/1987 | Le Van Mao et al. | 585/640 |
| 4,752,651 A | 6/1988 | Kaiser | 585/640 |
| 4,767,886 A | 8/1988 | Kawamura et al. | 585/640 |
| 4,777,321 A | 10/1988 | Harandi et al. | 585/640 |
| 4,861,938 A | 8/1989 | Lewis et al. | 585/640 |
| 4,912,281 A | 3/1990 | Wu | 585/640 |
| 5,043,503 A | 8/1991 | Del Rossi et al. | 585/360 |
| 5,053,374 A | 10/1991 | Absil et al. | 502/64 |
| 5,095,163 A | 3/1992 | Barger | 585/640 |
| 5,095,167 A | 3/1992 | Christensen | 585/720 |
| 5,110,776 A | 5/1992 | Chitnis et al. | 502/64 |
| 5,182,242 A | 1/1993 | Marler | 502/66 |

(List continued on next page.)

FOREIGN PATENT DOCUMENTS

| | | |
|---|---|---|
| EP | 0026 041 A1 | 4/1981 |
| EP | 0 882 692 A1 | 12/1998 |

OTHER PUBLICATIONS

Olson et al., *Chemical and Physical Properties of the ZSM–5 Substitutional Series*, Journal of Caralysis, 61, pp. 390–396 (1980).

Keim et al., *The Methanol–to–Gasoline (MTG) Process: Status Report on 100 BPD Fluid Bed Pilot Plant*, C–16, pp. 2–160–2–166.

Chang, "Methanol Conversion to Light Olefins," Catal. Rev.–Sci. Eng., 26(3&4), 323–345 (1984).

Kaeding et al., "Production of Chemicals from Methanol," Journal of Catalysis 61, 155–164 (1980).

Barger et al., "Converting Natural Gas to Ethylene and Propylene by the UOP/Hydro MTO Process," 12th International Zeolite Conference Materials Research Society p. 567–573 (1999).

Primary Examiner—Thuan D. Dang

(57) ABSTRACT

There is provided a process for converting methanol and/or dimethyl ether to a product containing $C_2$ to $C_4$ olefins which comprises the step of contacting a feed which contains methanol and/or dimethyl ether with a catalyst comprising a porous crystalline material. The contacting is conducted in the presence of a cofed aromatic compound under conversion conditions including a temperature of about 350° C. to about 550° C. and a methanol and/or dimethyl ether partial pressure less than or equal to 50 psia (345 kPa). The porous crystalline material used in the catalyst has a pore size greater than the critical diameter of the aromatic compound and a Diffusion Parameter for 2,2-dimethylbutane of about 0.1 to about 26 $sec^{-1}$ when measured at a temperature of 120° C. and a 2,2- dimethylbutane pressure of 60 torr (8 kPa), and the aromatic compound is capable of alkylation by the methanol and/or dimethyl ether under said conversion conditions.

19 Claims, No Drawings

U.S. PATENT DOCUMENTS

| | | | |
|---|---|---|---|
| 5,191,041 A | 3/1993 | Barger et al. | 585/640 |
| 5,191,142 A | 3/1993 | Marshall et al. | 585/640 |
| 5,231,064 A | 7/1993 | Absil et al. | 502/68 |
| 5,250,277 A | 10/1993 | Kresge et al. | 423/329.1 |
| 5,304,698 A | 4/1994 | Husain | 585/722 |
| 5,714,662 A | 2/1998 | Vora et al. | 585/640 |
| 5,714,663 A | 2/1998 | Serrand et al. | 585/648 |
| 6,040,257 A | 3/2000 | Drake et al. | 502/64 |
| 6,046,372 A | 4/2000 | Brown et al. | 585/640 |

PROCESS FOR PRODUCING LIGHT OLEFINS

RELATED APPLICATIONS

This application is a continuation-in-part of U.S. application Ser. No. 09/547,093, filed Apr. 11, 2000 now abandoned, the entire disclosure of which is expressly incorporated herein by reference which is a CIP of U.S. Ser. No. 09/055,486, filed Apr. 6, 1998, U.S. Pat. No. 6,046,372 which is a CIP of U.S. Ser. No. 08/725,277 filed Oct. 2, 1996, now abandoned.

FIELD OF THE INVENTION

The present invention relates to a process for producing light olefins rich in ethylene and propylene from methanol and dimethyl ether.

BACKGROUND TO THE INVENTION

A remarkable growth in the production of synthetic fibers, plastics and rubber has taken place in recent decades. This growth has, to a very large extent, been supported and encouraged by an expanding supply of inexpensive petrochemical raw materials such as ethylene, propylene, and other, four and five carbon olefins. Side by side with this growth, there has been an increasing demand for alkylate, made by reacting olefins with isobutane, for use as a high octane gasoline component.

Burgeoning demand for olefins, particularly ethylene, propylene and butenes, has of course led to periods of shortage, which has led to substantial price increases in the feedstocks to the commercialized technologies. These feedstocks are largely $C_2$ to $C_4$ olefins co-produced with natural gas and/or paraffinic straight run naphtha. These feedstocks tend to be substantially more expensive than methane, making it desirable to provide efficient means for converting methane to olefins.

Methane is an abundant low-value petrochemical feedstock. Methane is a less-expensive raw material than the ethane, LPG, and naphtha feedstock used today for the manufacture of ethylene and propylene. Although less expensive, methane is currently not used to produce light olefins because the manufacturing steps required are more expensive and/or less selective than the commercially utilized routes.

Conversion of methane to methanol, followed by conversion of methanol to ethylene and propylene appears to be the most attractive route to light olefins from methane. In this respect, it is known that methanol or dimethyl ether can be catalytically converted to olefin-containing hydrocarbon mixtures by contact under certain conditions with particular types of crystalline zeolite materials. For example, U.S. Pat. Nos. 4,025,575 and 4,038,889 both disclose processes whereby methanol and/or methyl ether can be converted to an olefin-containing product over a Constraint Index 1–12 zeolite catalyst, particularly ZSM-5. ZSM-5, in fact, converts methanol and/or dimethyl ether to hydrocarbons containing a relatively high concentration of light olefins with prolonged catalyst lifetime before catalyst regeneration becomes necessary.

It has also been reported that other types of zeolite catalysts can be used to convert methanol and/or dimethyl ether to olefin-containing hydrocarbons products containing even higher proportions of light olefins than obtained with ZSM-5. For example, U.S. Pat. No. 4,079,095 discloses that zeolites of the erionite-offretite-chabazite type, and especially ZSM-34, can usefully be employed to promote conversion of methanol and/or dimethyl ether to products comprising a major amount of ethylene and propylene. However, while enionite-offretite-chabazite type catalysts are highly selective to light olefins production, such smaller pore zeolites tend to age rapidly in comparison to ZSM-5 when used for methanol/dimethyl ether conversion.

U.S. Pat. Nos. 4,677,242 and 4,752,651 disclose the conversion of methanol to $C_2$–$C_4$ olefins over various silicoaluminophosphates and "non-zeolitic molecular sieves" (such as metal aluminophosphates) and teach that the addition of diluents, such as aromatic materials, having a kinetic diameter greater than the pore size of the molecular sieve increases the ethylene to propylene ratio in the product.

U.S. Pat. No 4,499,314 discloses that the addition of various promoters, including aromatic compounds, such as toluene, accelerates the conversion of methanol to hydrocarbons over zeolites, such as ZSM-5, which have a pore size sufficient to permit sorption and diffusion of the promoter. In particular, the U.S. Pat. No. 4,499,314 teaches that the increased conversion resulting from the addition of the promoter allows the use of lower severity conditions, particularly lower temperatures, to increase the yield of lower olefins (column 4, lines 17–22).

In contrast, U.S. Pat. No. 6,046,372 discloses that the addition of an aromatic cofeed allows the selective conversion of methanol to $C_2$ to $C_4$ olefins at relatively high temperatures (350 to 480° C.) and relatively high methanol partial pressures (15 to 150 psia) over a zeolite having a pore size greater than the critical diameter of the cofed aromatic compound.

According to the invention, it has now been found that improved ethylene and propylene selectivities can be achieved in the conversion of methanol by using the following combination of conditions: a zeolite catalyst with limited diffusivity, a cofed aromatic compound; high temperature; and a methanol partial pressure less than 50 psia. Methanol partial pressure can be reduced by a number of well known means, for example, by the addition of a diluent such as steam.

SUMMARY OF THE INVENTION

The present invention resides in a process for converting methanol and/or dimethyl ether to a product containing $C_2$ to $C_4$ olefins which comprises the step of contacting a feed which contains methanol and/or dimethyl ether with a catalyst comprising a porous crystalline material, said contacting step being conducted in the presence of a cofed aromatic compound under conversion conditions including a temperature of about 350° C. to about 550° C. and a methanol and/or dimethyl ether partial pressure less than or equal to 50 psia (345 kPa), said porous crystalline material having a pore size greater than the critical diameter of the aromatic compound and having a Diffusion Parameter for 2,2-dimethylbutane of about 0.1 to about 26 $sec^{-1}$ when measured at a temperature of 120° C. and a 2,2-dimethylbutane pressure of 60 torr (8 kPa), and the aromatic compound being capable of alkylation by the methanol and/or dimethyl ether under said conversion conditions.

Preferably, the molar ratio of methanol and/or dimethyl ether to aromatic compound is from 0.5:1 to 100:1, and more preferably from about 3:1 to about 30:1.

Preferably, the conversion conditions include a temperature of about 400° C. to about 500° C.

Preferably, the conversion conditions are such that the methanol conversion rate is less than 90% and more preferably less than 80%.

Preferably, the porous crystalline material has a pore size between 5 and 7 Angstrom.

Preferably, the porous crystalline material is an aluminosilicate zeolite and most preferably is ZSM-5.

Preferably, the porous crystalline material has a Diffusion Parameter for 2,2-dimethylbutane of about 0.1 to 15 sec$^{-1}$, and more preferably 0.2 to about 5 sec$^{-1}$, when measured at a temperature of 120° C. and a 2,2-dimethylbutane pressure of 60 torr (8 kPa).

Preferably, the catalyst has an alpha value less than 10 and more preferably less than 2.

DETAILED DESCRIPTION OF THE INVENTION

The present invention provides a process for selectively converting methanol and/or dimethyl ether to $C_2$–$C_4$ olefins, particularly propylene, over a catalyst comprising a porous crystalline material in the presence of a cofed aromatic compound which has a critical diameter less than the pore size of the catalyst and which is capable of alkylation by the methanol and/or dimethyl ether under the conditions of the conversion. The process of the invention uses a catalyst which comprises a porous crystalline material having restricted diffusivity, as measured by its Diffusion Parameter for 2,2-dimethylbutane, and operates at a temperature of about 350° C. to about 550° C. and a methanol and/or dimethyl ether partial pressure less than or equal to 50 psia (345 kPa).

As used herein, the Diffusion Parameter of a particular porous crystalline material is defined as $D/r^2 \times 10^6$, wherein D is the diffusion coefficient (cm$^2$/sec) and r is the crystal radius (cm). The required diffusion parameters can be derived from sorption measurements provided the assumption is made that the plane sheet model describes the diffusion process. Thus for a given sorbate loading Q, the value $Q/Q_{oO}$, where $Q_{oO}$ is the equilibrium sorbate loading and is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

In particular, the catalyst employed in the process of the invention comprises a porous crystalline material having a Diffusion Parameter for 2,2-dimethylbutane of 0.1 to 26 sec$^{-1}$, preferably 0.1 to 15 sec$^{-1}$ and more preferably 0.2 to 5 sec$^{-1}$, when measured at a temperature of 120° C. and a 2,2-dimethylbutane pressure of 60 torr (8 kPa).

The porous crystalline material employed in the process of the invention is also required to have a pore size greater than the critical diameter of the aromatic compound co-feed. For this reason, small pore molecular sieves, such as ZSM-34, are not suitable for use in the process of the invention. Preferred catalysts are porous crystalline materials having a pore size between 5 and 7 Angstrom and in particular intermediate pore size, aluminosilicate zeolites. One common definition for intermediate pore zeolites involves the Constraint Index test described in U.S. Pat. No. 4,016,218, the entire contents of which are incorporated herein by reference. In this case, intermediate pore zeolites have a Constraint Index of about 1–12, as measured on the zeolite alone without the introduction of modifiers and prior to any treatment to adjust the diffusivity of the catalyst. In addition to the medium-pore size aluminosilicates, other medium pore acidic metallosilicates, such as silicoaluminophosphates (SAPOs), can be used in the process of the invention.

Particular examples of suitable medium pore zeolites include ZSM-5, ZSM-1 1, ZSM-12, ZSM-22, ZSM-23, ZSM-35, ZSM48, and MCM-22, with ZSM-5 and ZSM-1 1 being particularly preferred.

Zeolite ZSM-5 and the conventional preparation thereof are described in U.S. Pat. No. 3,702,886, the disclosure of which is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. ZSM48 and the conventional preparation thereof is taught by U.S. Pat. No. 4,375,573, the disclosure of which is incorporated herein by reference. MCM-22 is disclosed in U.S.

Pat. Nos. 5,304,698 to Husain; 5,250,277 to Kresge et al.; 5,095,167 to Christensen; and 5,043,503 to Del Rossi et al., the disclosure of which patents are incorporated by reference.

As prepared commercially, unmodified intermediate pore size zeolites, such as ZSM-5, can have a Diffusion Parameter for 2,2-dimethylbutane ranging from 10 to 2000 sec$^{-1}$. The diffusivity required for the catalyst of the invention can be produced by a variety of previously disclosed synthetic strategies. One method to achieve the diffusivity required for the catalyst of the invention is severely steaming the catalyst so as to effect a controlled reduction in the micropore volume of the catalyst to not less than 50%, and preferably to 50–90%, of that of the unsteamed catalyst. Reduction in micropore volume is derived by measuring the n-hexane adsorption capacity of the catalyst, before and after steaming, at 90° C. and 75 torr n-hexane pressure. Steaming is effected at a temperature of at least about 850° C., preferably about 950 to about 1075° C., and most preferably about 1000 to about 1050° C. for about 10 minutes to about 10 hours, preferably from 30 minutes to 5 hours.

To effect the desired controlled reduction in micropore volume and diffusion parameter, it may be desirable to combine the catalyst, prior to steaming, with a phosphorus modifier. The amount of phosphorus modifier, as measured on an elemental basis, may be between about 0.05 and about 20 wt. %, and preferably is between about 1 and about 10 wt. %, based on the weight of the final catalyst.

Incorporation of the phosphorus modifier into the catalyst of the invention is conveniently achieved by the methods described in U.S. Pat. Nos. 4,356,338, 5,110,776 and 5,231,064, the entire disclosures of which are incorporated herein by reference. Treatment with phosphorus-containing compounds can readily be accomplished by contacting the porous crystalline material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt. %.

Representative phosphorus-containing compounds which may be used include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $RPS_2$, $RP(O)(OX)_2$, $RP(S)(SX)_2$, $R_2P(O)$ OX, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as phenyl radical, and X is hydrogen, R, or halide. These compounds include primary, $RPH_2$, secondary, $R_2PH$, and tertiary, $R_3P$, phosphines such as butyl phosphine, the tertiary phosphine oxides, $R_3PO$, such as tributyl phosphine oxide, the tertiary phosphine sulfides, $R_3PS$, the primary, $RP(O)(OX)_2$, and secondary, $R_2P(O)OX$, phosphonic acids such as benzene phosphonic acid, the corresponding sulfur derivatives such as $RP(S)(SX)_2$ and $R_2P(S)SX$, the esters of the phosphonic acids such as dialkyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites, and esters thereof such as the monopropyl ester, alkyl dialkylphosphinites, $(RO)PR_2$, and dialkyl alkyphosphinite, $(RO)_2PR$, esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$, and $(RS)_2PR$. Examples of phosphite esters include trimethylphosphite, triethylphosphite, diisopropylphosphite, butylphosphite, and pyrophosphites such as tetraethylpyrophosphate. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, $(RO)PCl_2$, dialkylphosphorochloridites, $(RO)_2PCl$, dialkylphosphinochloroidites, $R_2PCl$, alkyl alkylphosphonochloridates, $(RO)(R)P(O)Cl$, dialkyl phosphinochloridates, $R_2P(O)Cl$, and $RP(O)Cl_2$. Applicable corresponding sulfur derivatives include $(RS)PCl_2$, $(RS)_2PCl$, $(RS)(R)P(S)Cl$, and $R_2P(S)Cl$.

Particular phosphorus-containing compounds include ammonium phosphate, ammonium dihydrogen phosphate, diammonium hydrogen phosphate, diphenyl phosphine chloride, trimethylphosphite, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate, and other alcohol-$P_2O_5$ reaction products.

After contacting with the phosphorus-containing compound, the catalyst may be dried and calcined to convert the phosphorus to an oxide form. Calcination can be carried out in an inert atmosphere or in the presence of oxygen, for example, in air at a temperature of about 150° C. to about 750° C., preferably about 300° C. to about 500° C., for at least 1 hour, preferably 3 to 5 hours.

The porous crystalline material employed in the process of the invention may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. These materials, i.e., clays, oxides, etc., function as binders for the catalyst. It is desirable to provide a catalyst having good crush strength because in commercial use it is desirable to prevent the catalyst from breaking down into powder-like materials. These day and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 wt. % to about 80 wt. % of the composite.

Preferably, the binder material comprises silica or a kaolin clay.

Procedures for preparing silica-bound zeolites, such as ZSM-5, are described in U.S. Pat. Nos. 4,582,815; 5,053,374; and 5,182,242. A particular procedure for binding ZSM-5 with a silica binder involves an extrusion process.

The porous crystalline material may be combined with a binder in the form of a fluidized bed catalyst. This fluidized bed catalyst may comprise clay in the binder thereof, and may be formed by a spray-drying process to form catalyst particles having a particle size of 20 microns to 200 microns.

The catalyst employed of the invention preferably has a very low acid activity. Using the alpha test of acid activity disclosed in *Journal of Catalysis*, volume 61, page 395 (1980), for purposes of U.S. patent practice the entire disclosure of which is incorporated by reference herein, the catalyst of the invention preferably has an alpha value less than 10, more preferably less than 2. Where necessary, the alpha value of the catalyst can be reduced to the desired value by methods known in the art, such as steaming at temperatures of 350° C. to 500° C.

Any methanol feed comprising at least 60wt. % of methanol may be used to provide methanol for the use in this invention. Substantially pure methanol, such as industrial grade anhydrous methanol, is eminently suitable. Crude methanol, which usually contains from 12 wt. % to 20wt. % water, or even a more dilute solution, may also be used. Trace amounts (<1% by weight) of non-aromatic organic impurities, such as higher alcohols, aldehydes, or other oxygenated compounds have little effect on the conversion reaction of this invention and may be present in the methanol feed.

In place of, or in addition to methanol, the non-aromatic reactant feed may comprise dimethyl ether. When this component is present, it can comprise up to 100% of the non-aromatic organic reactant feed or dimethyl ether can be admixed with methanol to form the non-aromatic reactant feed. For purposes of the present invention, it is contemplated to directly convert methanol and/or methyl ether in the feed to a hydrocarbon mixture characterized by a high content of light olefins, especially ethylene. Such amounts of dimethyl ether as may be formed concomitantly in the conversion reaction, however, may be recovered and recycled with fresh organic reactant feed.

The process of the invention employs a methanol and/or dimethyl ether partial pressure less than or equal to 50 psia (345 kPa) and hence diluents can be added to the feed to reduce the methanol and/or dimethyl ether partial pressure to the required value. Suitable diluents include hydrogen, nitrogen, carbon dioxide, paraffins such as methane, ethane, propane, butanes, pentanes, hexanes, and heptanes, and water, with water being preferred.

The feed to the process of the invention also includes an aromatic compound which has a critical diameter less than the pore size of the zeolite catalyst and which is capable of alkylation by the methanol and/or dimethyl ether under the conditions of the conversion. The aromatic compound is believed to assist in the catalysis by reacting with the methanol to form alkylated aromatic intermediates which are cracked to olefins and the co-catalytic aromatic ring. The aromatic portion of the feedstock can come from a wide variety of sources. Even substantial amounts of non-aromatic organic components have little impact on the catalytic role of the aromatic co-feed. For this reason, any organic feedstream containing >10 wt. % aromatics, which have a critical diameter less than the pore size of the catalyst so as to be able to easily diffuse into the catalyst pores, is suitable for use in the process of the invention. These include, but are not limited to, benzene, toluene, xylenes, light reformates, full-range reformates or any distilled fraction thereof, coker naphtha or any distilled fraction thereof, FCC naphtha or any distilled fraction thereof, steam cracked naphtha or any distilled fraction thereof, and coal derived aromatics. Part of the required aromatic compound can also be produced in-situ by aromatization of the methanol feed, although in general some co-feeding of the aromatic compound with the methanol appears to be important. The presence of impurities, such as nitrogen and sulfur compounds, dienes and styrenes, in the aromatic component can be tolerated with little impact when fluid or moving bed embodiments of the invention are employed.

In a preferred embodiment, toluene comprises some or all of the aromatic portion of the feedstock.

The molar ratio of methanol and/or dimethyl ether to aromatic compound will normally be greater than 0.5:1, since higher concentrations of aromatic compound lead to excessive coking, increased volumes of separation and recycle traffic and minimal gains in total chemical selectivities. Moreover the molar ratio of methanol and/or dimethyl ether to aromatic compound is normally maintained below 100:1, since lower concentrations of aromatic compound lead to little or no noticeable improvement in the ethylene selectivity of the process. Preferably the molar ratio of methanol and/or dimethyl ether to aromatic compound is from about 3:1 to about 30:1.

The process of the invention is preferably carried out in a moving or fluid catalyst bed with continuous oxidative regeneration. The extent of coke loading can then be continuously controlled by varying the severity and/or the frequency of regeneration.

The process of the present invention is conducted at a temperature of about 350° C. to about 550° C., preferably of about 400° C. to about 500° C., and a methanol partial pressure less than 50 psia, preferably 5 psia to 20 psia. In addition, it is desirable that the conversion conditions are controlled so that the methanol conversion level is less than about 90% and preferably less than about 80% since, at higher conversion levels, competing reactions to aromatics methylation, such as olefin alkylation and/or oligomerization to produce $C_5+$ isoolefins and/or olefin conversion to aromatics and paraffins, lower the selectivity to ethylene and propylene. Suitable control of the methanol conversion can, of course, be achieved by variation of the weight hourly space velocity, which typically can vary from about 0.1 to about 100, preferably from about 0.1 to about 10.

The invention will now be more particularly described with reference to the following Examples.

In the Examples, the experiments were conducted in a downflow fixed-bed unit in which a 18 inch (46 cm) long, ½ inch (1.3 cm) outside diameter, quartz reactor with ⅛ inch (0.3 cm) outside diameter internal quartz thermowell was centered inside a 10 inch (46 cm) long, single-zone furnace. Methanol and aromatic feedstocks were obtained from Aldrich and used as received. Distilled water was produced in-house. The feeds were introduced using two Isco high-pressure positive displacement pumps. Aromatics and methanol were blended in the desired molar ratio and delivered from one pump, while the second pump was used to deliver the distilled water.

1/16 inch (16 mm) tubing was used to deliver each feedstock to a single, 250-cc vaporizer which was heat-traced and held at 220° C. Vaporized feed flowed from the vaporizer through the reactor, into a 300-cc product back-mixing vessel, through an on-line GC equipped with a 60-m DBWax column and an FID detector, and into a product collection can held at room temperature. Any gases produced flowed through the product collection can and finally through a wet test meter. All feed and product lines upstream of the GC sampling were held above 200° C. using heat tracing. The unit back-pressure was controlled with a Grove Loader. On-line total product GC was used to determine product composition.

EXAMPLE 1

Phosphoric acid, kaolin clay, and 450:1 SiO2/Al2O3 ZSM-5 were slurried in water and spray dried to make a typical fluid-bed catalyst. The catalyst was calcined in air at 510° C. The finished catalyst contained: 40 wt. % ZSM-5 and 4.5 wt. % phosphorus. This catalyst was then steamed at 1920° F. (1050° C.) for 0.75 hour, after which treatment it had an alpha of about 1, a diffusion parameter of 0.5, and a n-hexane sorption of 31 mg/g. This catalyst was used to convert a mixture of 75 wt. % water, 13 wt. % methanol and 12 wt. % p-xylene (methanol:xylene molar ratio of 3:1) at 430° C. and 1 atm. The hydrocarbon product selectivities are reported in Table 1.

EXAMPLE 2 (Comparative)

A typical fluid-bed catalyst was made by spray drying ZSM-34 and kaolin clay. The finished catalyst contained 40 wt % ZSM-34. This catalyst was then steamed at 1450° F. for 4 h, after which treatment it had an alpha of about 4. This catalyst was used to convert a mixture of 75 wt. % water and 25 wt. % methanol. The hydrocarbon product selectivities are reported in Table 1.

TABLE 1

| | Conditions | |
|---|---|---|
| Example | 2 | 1 |
| Catalyst | ZSM-34 | ZSM-5 |
| Temp. °C. | 430 | 430 |
| Pressure, atm | 1 | 1 |
| MeOH Conversion | 92 | 60 |
| Feed Composition, wt % | | |
| MeOH | 25 | 13 |
| Water | 75 | 75 |
| p-xylene | 0 | 12 |
| Product HC Selectivities, wt % | | |
| Coke | 5.7 | 0.1 |
| Methane | 6.9 | 0.6 |
| Ethane + Propane | 1.4 | 1.1 |
| Ethylene | 55.8 | 47.5 |
| Propylene | 22.9 | 36.1 |
| Butanes | 0.7 | 0.0 |
| Butenes | 4.5 | 6.6 |
| $C_5$—$C_9$ non-aromatic compounds | 2.0 | 1.8 |
| $C_8$—$C_{10}$ aromatic compounds | 0.0 | 6.2 |

The results in Table 1 demonstrate that use of p-xylene co-feed unexpectedly allows a ZSM-5 catalyst to produce higher selectivities of light olefins than the small pore ZSM-34 at comparable reaction conditions. The ZSM-5 catalyst makes less coke and methane than the ZSM-34 catalyst and has surprisingly improved stability.

What is claimed is:

1. A process for converting methanol and/or dimethyl ether to a product containing $C_2$ to $C_4$ olefins which comprises the step of contacting a feed which contains methanol and/or dimethyl ether with a catalyst comprising a porous crystalline material, said contacting step being conducted in the presence of a cofed aromatic compound under conversion conditions including a temperature of about 350° C. to about 550° C., a molar ratio of methanol and/or dimethyl ether to aromatic compound ranging from about 0.5:1 to 5:1, and a methanol and/or dimethyl ether partial pressure less than or equal to 345 kPa, said porous crystalline material having a pore size greater than the critical diameter of the aromatic compound and having a Diffusion Parameter for 2,2-dimethylbutane of about 0.1 to about 26 $sec^{-1}$ when measured at a temperature of 120° C. and a 2,2-dimethylbutane pressure of 8 kPa, and the aromatic compound being capable of alkylation by the methanol and/or dimethyl ether under said conversion conditions to provide a stream which contains $C_2$ to $C_4$ olefins.

2. The process of claim 1 wherein the molar ratio of methanol and/or dimethyl ether to aromatic compound is from about 0.5:1 to about 100:1.

3. The process of claim 1 wherein the molar ratio of methanol and/or dimethyl ether to aromatic compound is from about 3:1 to about 30:1.

4. The process of claim 1 wherein the aromatic compound is selected from the group consisting of benzene, toluene, xylenes, steam cracked naphthas or any distilled fraction thereof, full-range reformates or any distilled fraction thereof, coker naphtha or any distilled fraction thereof, FCC naphtha or any distilled fraction thereof, and coal derived aromatics.

5. The process of claim 1 wherein the conversion conditions include a temperature of about 400° C. to about 500° C.

6. The process of claim 1 wherein the conversion conditions are such that the methanol conversion rate is less than 90%.

7. The process of claim 1 wherein the porous crystalline material has a pore size of 5 to 7 Angstrom.

8. The process of claim 1 wherein the porous crystalline material is ZSM-5.

9. The process of claim 1 wherein the porous crystalline material has a Diffusion Parameter for 2,2-dimethylbutane of about 0.1 to about 15 $sec^{-1}$ when measured at a temperature of 120° C. and a 2,2-dimethylbutane pressure of 60 torr (8 kPa).

10. The process of claim 1 wherein the porous crystalline material has a Diffusion Parameter for 2,2-dimethylbutane of about 0.2 to about 5 $sec^{-1}$, when measured at a temperature of 120° C. and a 2,2-dimethylbutane pressure of 60 torr (8 kPa).

11. The process of claim 1 wherein the porous crystalline material is ZSM-5 with a Diffusion Parameter for 2,2-dimethylbutane of about 0.1 to about 15 $sec^{-1}$, when measured at a temperature of 120° C. and a 2,2-dimethylbutane pressure of 60 torr (8 kPa).

12. The process of claim 1 wherein the porous crystalline material is ZSM-5 with a Diffusion Parameter for 2,2-dimethylbutane of about 0.2 to about 5 $sec^{-1}$, when measured at a temperature of 120° C. and a 2,2-dimethylbutane pressure of 60 torr (8 kPa).

13. The process of claim 1 wherein the catalyst has an alpha value less than 10.

14. The process of claim 1 wherein the catalyst has an alpha value less than 2.

15. A process for converting methanol and/or dimethyl ether to a product containing $C_2$ to $C_4$ olefins which comprises:

steaming a catalyst comprising a porous crystalline material at a temperature of at least about 850° C. for about 10 minutes to about 10 hours; and contacting a feed which contains methanol and/or dimethyl ether with said catalyst, wherein said contacting step is conducted in the presence of a cofed aromatic compound under conversion conditions including a temperature of about 350° C. to about 550° C., wherein a molar ratio of methanol and/or dimethyl ether to aromatic compound ranges from about 0.5:1 to 5:1, wherein a methanol and/or dimethyl ether partial pressure is less than or equal to 345 kPa, wherein said porous crystalline material has a pore size greater than the critical diameter of the aromatic compound and has a Diffusion Parameter for 2,2-dimethylbutane of about 0.1 to about 26 $sec^{-1}$ when measured at a temperature of 120° C. and a 2,2-dimethylbutane pressure of 8 kPa, and wherein the aromatic compound is capable of alkylation by the methanol and/or dimethyl ether under said conversion conditions to provide a stream which contains $C_2$ to $C_4$ olefins.

16. The process of claim 15 wherein the porous crystalline material has a Diffusion Parameter for 2,2-dimethylbutane of about 0.1 to about 15 $sec^{-1}$, when measured at a temperature of 120° C. and a 2,2-dimethylbutane pressure of 60 torr (8 kPa).

17. The process of claim 15 wherein the porous crystalline material has a Diffusion Parameter for 2,2-dimethylbutane of about 0.2 to about 5 $sec^{-1}$, when measured at a temperature of 120° C. and a 2,2-dimethylbutane pressure of 60 torr (8 kPa).

18. The process of claim 15 wherein the catalyst has an alpha value less than 10.

19. The process of claim 15 wherein the catalyst has an alpha value less than 2.

* * * * *